US012599715B2

(12) United States Patent
Ariagno et al.

(10) Patent No.: US 12,599,715 B2
(45) Date of Patent: Apr. 14, 2026

(54) SYRINGE STABILIZER

(71) Applicant: Takeda Pharmaceutical Company Limited, Osaka (JP)

(72) Inventors: Scott Richard Ariagno, Inverness, IL (US); Angela Teresa Muriset, Hoffman Estates, IL (US); Daniel Edward Roush, Niles, IL (US); Denise A. Alexander, Naperville, IL (US); Madeleine Clare Gibson, Madison, WI (US); Gin-Fu Chen, Newton, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 142 days.

(21) Appl. No.: 18/603,079

(22) Filed: Mar. 12, 2024

(65) Prior Publication Data

US 2024/0216603 A1     Jul. 4, 2024

Related U.S. Application Data

(62) Division of application No. 16/310,916, filed as application No. PCT/US2017/039260 on Jun. 26, 2017, now Pat. No. 11,957,867.

(Continued)

(51) Int. Cl.
A61M 5/00          (2006.01)
A61M 5/31          (2006.01)
(Continued)

(52) U.S. Cl.
CPC .......... A61M 5/008 (2013.01); A61M 5/3129 (2013.01); A61M 5/315 (2013.01);
(Continued)

(58) Field of Classification Search
CPC .......... A61M 25/02; A61M 2025/0206; A61M 2025/022; A61M 2025/0226;
(Continued)

(56) References Cited

U.S. PATENT DOCUMENTS 3,625,210 A * 12/1971 Mikkelson ............ A61M 25/02
                                                          128/877
4,586,691 A     5/1986 Kozlow
(Continued)

FOREIGN PATENT DOCUMENTS

AR          033619 A1   12/2003
AR          042241 A     6/2005
(Continued)

OTHER PUBLICATIONS

EP 17735352.1, Jul. 1, 2020, European Communication Report.
(Continued)

*Primary Examiner* — Kevin C Sirmons
*Assistant Examiner* — Alexandra Lalonde
(74) *Attorney, Agent, or Firm* — Wolf, Greenfield & Sacks, P.C.

(57)          ABSTRACT

A syringe stabilizing apparatus has a base and a syringe support. The syringe support is vertically disposed above the base, elevating a fluid-filled portion of an infusion set vertically above the base and orienting a delivery end of the fluid-filled portion upwardly relative to a horizontal plane to take advantage of a gravitational effect on a fluid during delivery of the fluid from the fluid-filled portion to a patient. The syringe support comprises a first retainer and a selectively actuated tube clamp. The first retainer has an opening in which a rigid portion of the infusion set is received and retained therein without further user intervention. The selectively actuated tube clamp is operatively aligned with the first retainer. A flexible tube extending from the rigid portion (Continued)

of the infusion set extends through the selectively actuated tube clamp.

19 Claims, 10 Drawing Sheets

Related U.S. Application Data

(60) Provisional application No. 62/354,964, filed on Jun. 27, 2016.

(51) Int. Cl.
   *A61M 5/315*      (2006.01)
   *A61M 25/02*      (2006.01)

(52) U.S. Cl.
   CPC ............... *A61M 2005/3139* (2013.01); *A61M 2025/024* (2013.01); *A61M 2025/028* (2013.01); *A61M 2205/586* (2013.01)

(58) Field of Classification Search
   CPC .... A61M 2025/0233; A61M 2025/024; A61M 2025/0246; A61M 2025/0253; A61M 2025/026; A61M 2025/0266; A61M 2025/0273; A61M 2025/028; A61M 2025/0286; A61M 2025/0213; A61M 5/008; A61M 5/3129; A61M 5/315; A61M 5/3137; A61M 5/1415; A61M 5/1418; A61M 5/14; A61M 5/46; A61M 2005/3139; A61M 2005/1416; A61M 2005/1401; A61M 2205/586; A61M 39/28; A61M 39/287; A61M 39/283; A61M 39/284; A61M 39/285; A61M 39/286; A61M 39/288; A61M 39/281; A61M 39/26; A61M 2039/0673; A61M 2209/08; A61M 2209/084; Y10T 24/44752; A61J 15/0053
   See application file for complete search history.

(56) References Cited

U.S. PATENT DOCUMENTS

| | | | |
|---|---|---|---|
| 4,643,389 | A | 2/1987 | Elson et al. |
| 4,737,151 | A | 4/1988 | Clement et al. |
| 4,960,259 | A | 10/1990 | Sunnanväder et al. |
| 5,458,581 | A * | 10/1995 | Hull .................... A61M 39/285 |
| | | | 251/9 |
| 5,741,227 | A | 4/1998 | Sealfon |
| 5,779,675 | A | 7/1998 | Reilly et al. |
| 6,086,564 | A * | 7/2000 | McLaughlin ......... A61M 25/02 |
| | | | 604/179 |
| 6,361,016 | B1 | 3/2002 | Schulz |
| 6,439,927 | B1 | 8/2002 | Peter et al. |
| 6,581,648 | B1 | 6/2003 | Zolentroff et al. |
| 9,717,885 | B1 | 8/2017 | Narciso Martinez et al. |
| 11,957,867 | B2 | 4/2024 | Ariagno et al. |
| 2002/0161333 | A1 * | 10/2002 | Luther .................. A61M 39/26 |
| | | | 604/167.01 |
| 2006/0167415 | A1 | 7/2006 | Nemoto |
| 2008/0102115 | A1 | 5/2008 | Oyhenart et al. |
| 2010/0030160 | A1 | 2/2010 | Glocker |
| 2010/0063447 | A1 | 3/2010 | Stempfle et al. |
| 2010/0197205 | A1 | 8/2010 | Ohnishi |
| 2010/0229354 | A1 | 9/2010 | Werth |
| 2010/0232490 | A1 | 9/2010 | Balakrishnan et al. |
| 2010/0286609 | A1 | 11/2010 | Mahurkar |
| 2012/0130305 | A1 | 5/2012 | Bonnal et al. |
| 2012/0197205 | A1 | 8/2012 | Peters |
| 2012/0232490 | A1 | 9/2012 | Andino |
| 2012/0265098 | A1 | 10/2012 | McGhie |
| 2013/0158506 | A1 | 6/2013 | Harris et al. |
| 2014/0066862 | A1 * | 3/2014 | Schweers ............ A61M 5/3137 |
| | | | 604/227 |
| 2014/0163365 | A1 | 6/2014 | Shaffer et al. |
| 2014/0330247 | A1 | 11/2014 | Rosenberg et al. |
| 2015/0088075 | A1 | 3/2015 | Khalaj |
| 2015/0258284 | A1 | 9/2015 | Fenster et al. |
| 2015/0328406 | A1 | 11/2015 | Dunne |
| 2019/0321542 | A1 | 10/2019 | Ariagno et al. |
| 2023/0355890 | A1 * | 11/2023 | Moleda .............. A61M 5/3271 |

FOREIGN PATENT DOCUMENTS

| | | |
|---|---|---|
| CN | 1193917 A | 9/1998 |
| CN | 2553815 Y | 6/2003 |
| CN | 1431918 A | 7/2003 |
| CN | 1671428 A | 9/2005 |
| CN | 101011287 A | 8/2007 |
| CN | 101146561 A | 3/2008 |
| CN | 101296727 A | 10/2008 |
| CN | 102186518 A | 9/2011 |
| CN | 102438682 A | 5/2012 |
| JP | 61-262271 A | 11/1986 |
| JP | 2001-523490 A | 11/2001 |
| JP | 2002-165879 A | 6/2002 |
| JP | 2003-533245 A | 11/2003 |
| JP | 2004-065736 A | 3/2004 |
| JP | 3119004 U | 2/2006 |
| JP | 2008-302237 A | 12/2008 |
| JP | 2010-519383 A | 6/2010 |
| JP | 2011-072345 A | 4/2011 |
| JP | 2014-159479 A | 9/2014 |
| JP | 2015-501137 A | 1/2015 |
| JP | 2016-047477 A | 4/2016 |
| KR | 10-2012-0094827 A | 8/2012 |
| MX | 2013008440 A | 1/2015 |
| NL | 1040359 C2 | 3/2015 |
| RU | 2013104397 A | 8/2014 |
| TW | I688417 B | 3/2020 |
| WO | WO 97/07838 A1 | 3/1997 |
| WO | WO 98/48872 A1 | 11/1998 |
| WO | WO 99/55409 A1 | 11/1999 |
| WO | WO 2001/039820 A1 | 6/2001 |
| WO | WO 01/62328 A1 | 8/2001 |
| WO | WO 2005/102416 A1 | 11/2005 |
| WO | WO 2010/127146 A1 | 11/2010 |
| WO | WO 2010/132837 A1 | 11/2010 |
| WO | WO 2012/159211 A1 | 11/2012 |

OTHER PUBLICATIONS

EP 21167025.2, Nov. 22, 2021, Extended European Search Report.
PCT/US2017/039260, Nov. 11, 2017, International Search Report and Written Opinion.
PCT/US2017/039260, Jan. 10, 2019, International Preliminary Report on Patentability.
European Communication Report dated Jul. 1, 2020 for European Application No. EP 17735352.1.
Extended European Search Report dated Nov. 22, 2021 for European Application No. EP 21167025.2.
International Search Report and Written Opinion mailed Oct. 11, 2017 for International Application No. PCT/US2017/039260.
International Preliminary Report on Patentability mailed Jan. 10, 2019 for International Application No. PCT/US2017/039260.

\* cited by examiner

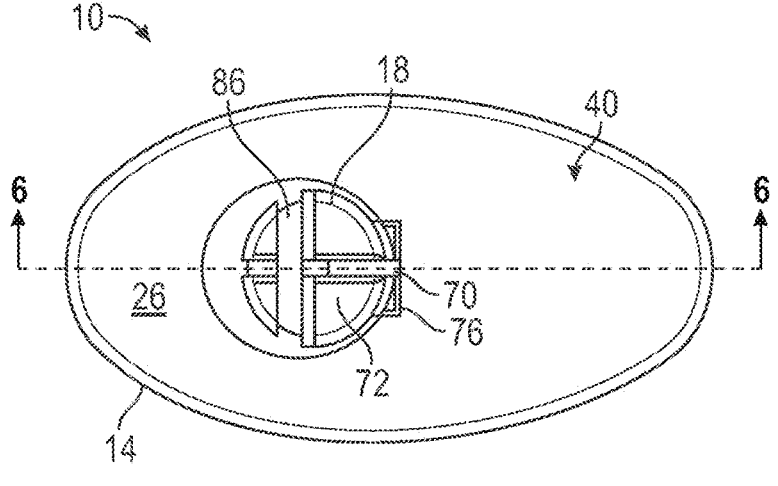
FIG. 4
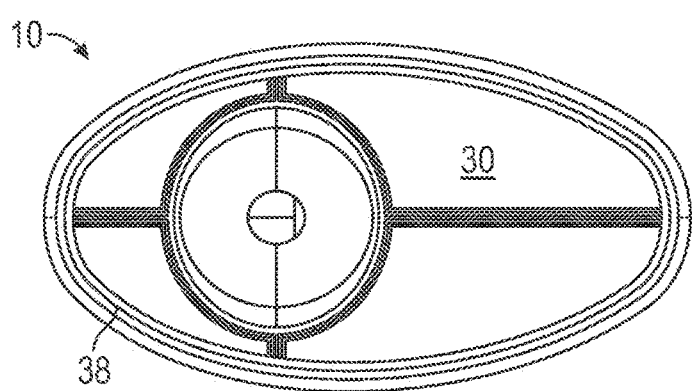
FIG. 5
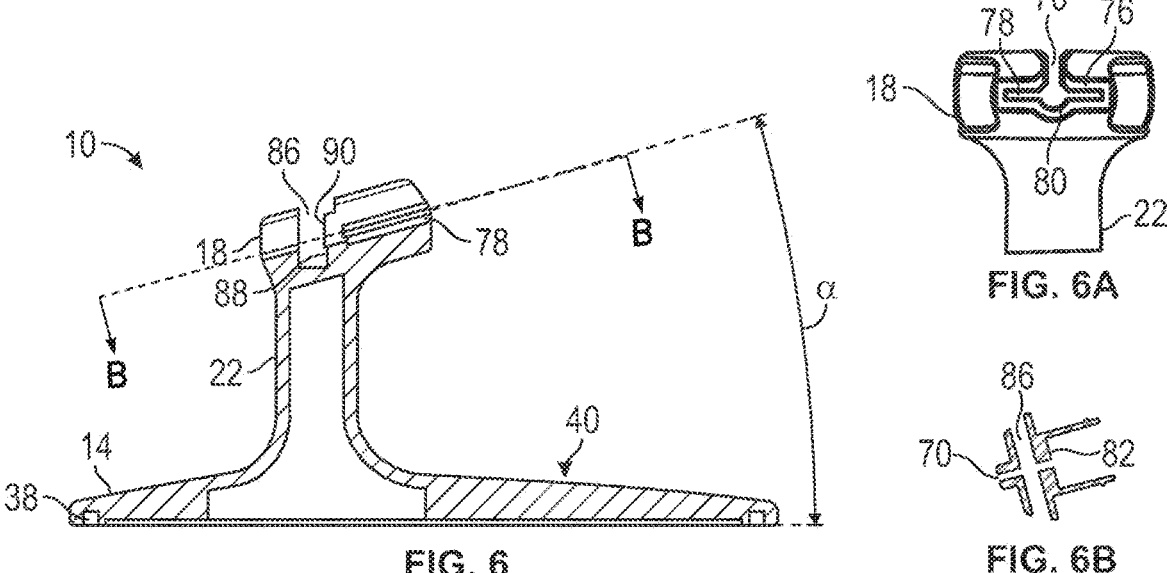
FIG. 6
FIG. 6A
FIG. 6B

SYRINGE STABILIZER

This application is a divisional of U.S. application Ser. No. 16/310,916, filed Dec. 18, 2018, now U.S. Pat. No. 11,957,867, which is a national stage filing under 35 U.S.C. § 371 of International Application No. PCT/US2017/039260, filed Jun. 26, 2017, which claims the benefit of U.S. Provisional Application No. 62/354,964, filed Jun. 27, 2016. The contents of these applications are incorporated herein by reference in their entirety.

BACKGROUND

Patients afflicted with certain diseases are often required to receive frequent therapy delivered by an infusion set into the patient's arm, including his/her hand. During this therapy, a fluid-filled syringe contains a medical treatment that is delivered via medical tubing to the patient through a needle or cannula.

Bleeding disorders, and particularly congenital or acquired deficiencies in coagulation factors, are typically treated by factor replacement. Congenital coagulation disorders include hemophilia, a recessive X-linked disorder involving a deficiency of coagulation Factor VIII (hemophilia A) or Factor IX (hemophilia B), and von Willebrand's disease, a rare bleeding disorder involving a severe deficiency of von Willebrand Factor. Hemophilia C is a milder form of hemophilia caused by a deficiency in Factor XI. It is usually asymptomatic, but factor replacement therapy may be required during surgery. Acquired coagulation disorders may arise in individuals without a previous history of bleeding as a result of a disease process. For example, acquired coagulation disorders may be caused by inhibitors or autoimmunity against blood coagulation factors, such as Factor VIII, von Willebrand Factor, Factors IX, V, XI, XII and XIII; or by hemostatic disorders such as caused by liver disease, which may be associated with decreased synthesis of coagulation factors. Conventional therapy for hemophilia A and Factor VIII inhibitor patients is accomplished by therapeutics like recombinant Factor VIII (rFVIII) or procoagulant bypassing agents, for example FEIBA or recombinant Factor Vila. Conventional therapy for von Willebrand's disease is accomplished by therapeutics like recombinant von Willebrand Factor (rVWF).

Some intravenous biologic treatments require administration of multiple consecutive syringes to achieve a desired dose or therapeutic regimen. This could occur 1) because of high fluid volume, 2) when a biologic's properties are negatively impacted by pooling into a single syringe, or 3) when multiple biologic products must be co-administered without pooling into a single syringe.

With increasing frequency, self-administration of biologics in a home setting is preferred over administration by healthcare professionals in a clinical setting. Empowering patients is both cost-effective and reduces overall impact to patient lives. However, the unique case of intravenous administration of multiple syringes presents an ergonomic challenge for patients that self-administer. Once an infusion needle is inserted into a peripheral vein, for example into the hand, performing tasks with that hand becomes difficult. Continued use of that hand may cause significant discomfort or cause the needle to slip out of position.

For example, a single therapy session for von Willebrand's disease typically requires multiple syringes, each filled with the pharmaceutical composition comprising rVWF to be delivered to the patient. For patients who self-administer their therapeutic doses, recharging the syringe or swapping out a syringe attached to the infusion set during therapy can be difficult because the needle or cannula is inserted into the patient's arm, thus limiting the use of that arm during therapy.

SUMMARY

Systems and methods for administration of therapeutic fluid are provided. Certain of the systems and methods described herein permit a single user to intravenously administer therapeutic fluid to himself/herself. The subject matter of the present invention involves, in some cases, interrelated products, alternative solutions to particular problem, and/or a plurality of different uses of one or more systems and/or articles.

According to one aspect, a syringe stabilizing apparatus is provided. The syringe stabilizing apparatus includes a base and a syringe support. The syringe support is vertically disposed above the base, elevating a fluid-filled portion of an infusion set vertically above the base and orienting a delivery end of the fluid-filled portion upwardly relative to a horizontal plane to take advantage of a gravitational effect on a fluid during delivery of the fluid from the fluid-filled portion to a patient. The syringe support includes a first retainer and a selectively actuated tube clamp. A rigid portion of the infusion set is received and retained within an opening in the first retainer without further user intervention. In some embodiments, the selectively actuated tube clamp is operatively aligned with the first retainer wherein a flexible tube extending from the rigid portion of the infusion set extends through the tube clamp. A user's first arm is used to release the selectively actuated tube clamp to allow a flow of the fluid from the delivery end of the fluid-filled portion, while a user's second arm remains substantially motionless and provides a stabilizing force against the base as the user receives the flow of fluid into the second arm.

In some embodiments, the first retainer is a longitudinal slot in an upper surface of the syringe support which frictionally engages the rigid portion of the infusion set with a resistant force sufficient to secure a syringe barrel joined to the rigid portion of the infusion set as a plunger disposed within the barrel is forced downwardly towards the delivery end. The syringe support may include a transverse slot intersecting the longitudinal slot so that the tube clamp resides within and is slidable within the transverse slot. The tube clamp may include a tube receiver having an opening alignable with the longitudinal slot and a clamping section generally transverse to the longitudinal slot. The clamping section may have a cross-sectional area configured for pinching a flexible tube of the infusion set as the tube clamp is slid within the longitudinal slot in a direction transverse to the longitudinal slot. A cross-sectional area of the clamping section may be less than a cross-sectional area of the tube receiver. The transverse slot may have a concave recess extending in a direction parallel to a length of the transverse slot and wherein the tube clamp has a convex keeper snap fit within the recess and traversable in the slot during actuation of clamping and releasing of the flexible tube within the tube clamp. The longitudinal slot may have a first segment having a first transverse cross-sectional area configured for receiving and retaining the rigid portion of the infusion set and a second segment having a second transverse cross-sectional area configured to receive and retain the flexible tube.

In some embodiments, the transverse slot may intersect the second segment of the longitudinal slot. The base may be portable and may include an ergonomic handset such that the user stabilizes the syringe stabilizing apparatus against a work surface with the second hand by engaging the ergonomic handset.

In some embodiments, the ergonomic handset may be located on an upper surface of the base having a surface area greater than a surface area of an upper surface of the syringe support. The base may have an engagement surface sized and shaped to be supported by a generally planar work surface on which the user's second arm rests. To simplify production, the syringe support is integrally joined with the base by a vertically oriented stem. The syringe support may further include an upper surface having a longitudinal slot therein configured to accept a portion of an infusion set and retain the portion of the infusion set.

In some embodiments, a syringe barrel of the infusion set is oriented at an angle above a horizontal axis such that a delivery end of the syringe barrel is vertically offset below a syringe plunger and the syringe barrel is retained in an elevated position relative to the base. The angle may be greater than 5 degrees and less than 90 degrees. Frictional engagement between the portion of the infusion set and the longitudinal slot is sufficient to maintain a position and an orientation of the syringe barrel as a plunger disposed within the barrel is forced downwardly towards the delivery end. The syringe stabilizing apparatus also includes a removable fitting receiver within the syringe support having slots configured to receiving and retaining portions of an infusion set fitting.

According to another aspect, a syringe stabilizing apparatus includes a portable base and a syringe support. The portable base has an engagement surface supporting the syringe stabilizer against a work surface and an ergonomic handset. Vertically disposed above the base, the syringe support includes a first channel, a second channel, and a selectively actuated tube clamp. In the first channel, a lengthwise opening is configured to accept a portion of an infusion set and retain the portion of the infusion set so that a syringe barrel of the infusion set is oriented at an angle above a horizontal axis. In this configuration, a delivery end of the syringe barrel is vertically offset below a syringe plunger and the syringe barrel is retained in an elevated position relative to the base. Furthermore, the referred angle is greater than 5 degrees and less than 90 degrees. Also, the second channel is transverse to and intersects the first channel, and the tube clamp is slidably disposed within the second channel. The tube clamp includes a tube receiver having an opening alignable with the first channel and a clamping section generally transverse to the first channel. A cross-sectional area of the clamping section is configured for pinching a flexible tube of the infusion set as the tube clamp is slid within the second channel in a direction transverse to the first channel.

In some embodiments, the tube clamp is releasable by a user's first arm to allow a flow of the fluid from the delivery end of the barrel of the syringe while the user's second arm remains substantially motionless. In addition, the stabilizer provides a stabilizing force against the ergonomic handset of the base as the user receives the flow of fluid into the second arm. The syringe support may be integrally joined with the base by a vertically oriented stem forming a single-piece, uni-body construction therewith. The syringe stabilizing may further comprise a removable fitting receiver within the syringe support having slots configured to receiving and retaining portions of an infusion set fitting therein.

According to yet another aspect, the present syringe stabilizing apparatus includes a base and a syringe support. The syringe support is vertically disposed above the base, elevating a fluid-filled portion of an infusion set vertically above the base and angling the fluid-filled portion upwardly at an angle less than 90 degrees relative to a horizontal plane to take advantage of a gravitational effect on a fluid during delivery of the fluid from the fluid-filled portion to a patient. The syringe support may include a first retainer and a selectively actuated tube clamp. An opening in the first retainer may receive and retain a rigid portion of the infusion set without further user intervention. The selectively actuated tube clamp may be operatively aligned with the first retainer so that a flexible tube extending from the rigid portion of the infusion set extends through the tube clamp. An arrangement of the base and syringe support respective positions may orient and retain the fluid-filled portion of the infusion set such that a patient who is self-administering a therapeutic fluid is able to manipulate the tube clamp and the fluid-filled portion with a first arm while receiving the therapeutic fluid into a second arm via the infusion set as the second arm remains substantially motionless and provides a stabilizing force against the base.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 4 is a top plan view of the syringe stabilizer of FIG. 2;

FIG. 5 is a bottom plan view of the syringe stabilizer of FIG. 2;

FIG. 6 is a cross-sectional view of the syringe stabilizer of FIG. 2 taken along axis 6-6 of FIG. 4;

FIG. 6A is a rear view of a syringe support of the syringe stabilizer of FIG. 2;

FIG. 6B is a cross-sectional view taken along axis B-B shown in FIG. 6;

DETAILED DESCRIPTION

Figure 1:
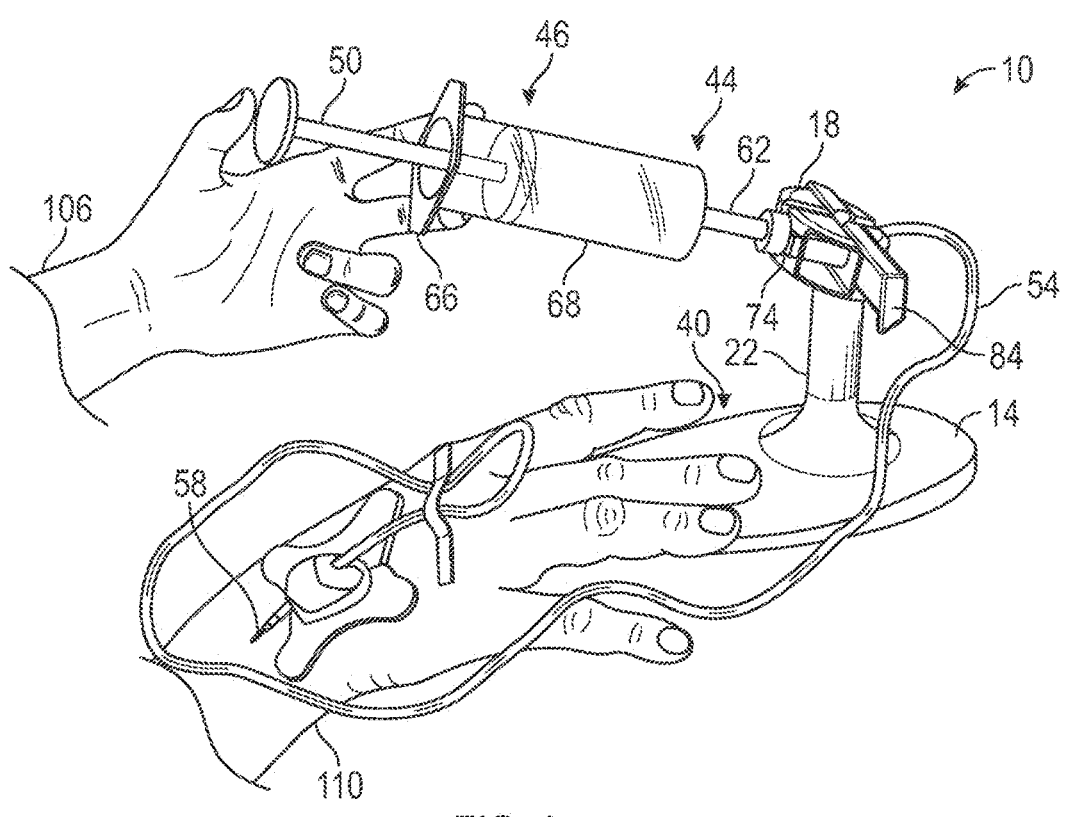
FIG. 1 is a perspective view of a syringe stabilizer according to one aspect in use with a tube clamp in an open condition to allow flow of a therapeutic fluid from a syringe barrel to a patient.

Some aspects of the invention relate to the administration of therapeutic fluid. According to some aspects, an apparatus that allows a single user to intravenously administer therapeutic fluid to himself/herself is provided.

Described herein is a syringe stabilizer provided, in some embodiments, to solve the problems discussed above and other problems, and to provide advantages and aspects not provided by prior therapeutic delivery devices. A full discussion of the features and advantages of the present syringe stabilizer is deferred to the following detailed description, which proceeds with reference to the accompanying drawings.

Referring generally to the figures, syringe stabilizing apparatuses, or simply syringe stabilizers, 10 are illustrated. The syringe stabilizer 10 has a base 14 and a syringe support 18 vertically disposed above the base 14, generally by a stem 22 or other structure suitable for attaining the desired position relative to a work surface as will be explained in more detail below. In one embodiment, the syringe support 18 is integrally joined with the base 18 by the vertically oriented stem or arm 22 forming a single-piece, uni-body, monolithic construction.

According to one aspect, in some embodiments, a general purpose of the syringe stabilizer 10 is to allow a patient or user to self-administer a fluid therapy or medicine through an infusion set while keeping a first arm relatively motionless or still while manipulating the medicine-carrying syringe using a second arm. In this way, the syringe stabilizers 10 may elevate, support, and orient a medicine-carrying vessel (i.e. a syringe) while also regulating medicine delivery therefrom. These syringe stabilizers 10 may be ergonomic, generally portable, and configured, as in sized, shaped, and structured, for tabletop use.

In some embodiments, the stem 22 sets the height of the syringe stabilizer 10. The height of the syringe stabilizer is generally chosen to place a syringe at a comfortable user level where the user can actuate a plunger on the syringe while a needle or cannula from an infusion set is within an arm of the patient/user. In some embodiments, the height of the syringe stabilizer may between 2 inches and 10 inches (5.1 cm to 25.4 cm).

In an embodiment illustrated in FIGS. 2-6, the base 14 has an upper surface 26 and an opposite lower surface 30. In this embodiment, the base 14 has an oval shape, which may be an ovate oval shape, and further may be a broad ovate shape as illustrated. This base 14 shape has a length greater than a width to provide stability, and the broad ovate shape shown in FIGS. 2-6 has a major axis and a minor axis which intersect approximately at the stem 22.

The lower surface 30 has a ring 34 within a seat 38. The ring 34 may be produced from a softer elastic material which increases friction between the base 14 and a work surface upon which the base 14 is supported. The ring may be secured to the base by friction or mechanical fit, adhesive bonding, welding, or multi-shot molding. Thus, the ring 34 may provide an engagement surface against the work surface, which is generally planar and horizontally oriented so that a user may rest his/her arm thereon.

In some embodiments, the upper surface 26 may have an ergonomic feature or handset 40. This ergonomic feature 40 is located such that a user can brace, support, or steady the syringe stabilizer 10 during use. The ergonomic feature 40 illustrated in FIGS. 2-6 is provided by the ovate shape of the base 14. The ovate shape naturally expands the surface area of the upper surface 26 along the major axis forming a duckbill or tongue which is easily accessed by a user's hand or arm to provide a force against the upper surface 26 to brace the syringe stabilizer against unwanted or undesirable movement during use. Here, the upper surface 26 of the base 14 has a surface area greater than a surface area of an upper surface of syringe support 18.

In other embodiments, which are illustrated in FIGS. 7-18, the ergonomic feature or handset is one or more finger receivers, such as finger rings 42.

The syringe support 18 according to the embodiments illustrated in FIGS. 2-21 is structurally configured to maintain an infusion set 44 in a desired position throughout a therapeutic delivery of the fluid to a user or patient. This includes retaining a syringe 46 while the user actuates a plunger 50 to force fluid from the syringe barrel through tubing 54 and into the user via a cannula or needle 58.

As shown in FIGS. 2-15 and 19-21, the syringe support 18 may orient the syringe 46 at an angle such that a delivery end 62 of the syringe 46 is positioned at a vertical height above the base 14 that is lower than a vertical height above the base of an opposing end 66 through which the plunger 50 is inserted. This positioning takes advantage of gravitational effect while placing the plunger 50 in a location and position that is advantageous for the user in accessing and actuating the plunger 50 in terms of comfort and ease of use, ergonomically speaking.

In some embodiments, the syringe support 18 has a retainer such as a first channel in which a rigid portion of the infusion set 44 is received. The first channel is configured to accept and retain this rigid portion of the infusion set 44, generally the delivery end 62 of the syringe 46 or a fitting, by frictional engagement, such as a snap fit arrangement. The first channel's configuration may orient a syringe barrel 68 of the infusion set 44 at an angle above a horizontal axis such that the delivery end 62 of the syringe 46 is vertically offset below the syringe plunger 50, and the syringe barrel 68 is retained in an elevated position relative to the base 14 wherein the angle a is greater than 5 degrees and less than 90 degrees, in some embodiments between 5 degrees and 75 degrees, and in some embodiments about 15 degrees.

As illustrated in FIGS. 2-21, in some embodiments, the first channel is a longitudinal first slot 70 in an upper surface 72 of the syringe support 18. Accordingly, the first slot 70 has a lengthwise opening configured to accept a portion of an infusion set, typically a narrow extension of a fitting 74, such as a tube connector, attached to the syringe barrel 68 such as a Luer-type fitting. The first slot 70 may be tapered such that its shape is complementary to a shape of the narrow extension of the fitting. In one embodiment, the first slot 70 has a first segment having a first transverse cross-sectional area configured to receive and retain the rigid portion of the infusion set 44 therein and a second segment having a second transverse cross-sectional area configured to receive and retain the flexible tube 54 therein.

As illustrated, for example in FIG. 6A, in some embodiments, a fitting receiver 76 may be located within the first channel or in communication therewith to further retain the syringe 46 within the syringe support 18. The fitting receiver 76 is configured, as in sized and shaped, to receive portions of the fitting. For example, the fitting receiver 76 illustrated has opposing slots 78 separated by a center arcuate section 80. This arrangement of the fitting receiver 76 complements a winged fitting 74 wherein opposing wings located on the fitting 74 can be inserted within the slots 78 while an arcuate center segment of the fitting 74 is received within the arcuate section 80 of the fitting receiver 76. This fitting receiver 76 may be provided as a removable insert which is snap-fit within the syringe support 18 wherein the fitting receiver 76 may be swapped out with a different fitting receiver 74 to accept structurally diverse infusion set fittings 74. For example, the slots 78 and arcuate section 80 of the fitting receiver 76 can be configured, as in sized, oriented and shaped, to accept a particular infusion set fitting 74 (compare FIGS. 16 and 19).

As illustrated in FIG. 6B, in some embodiments, a raised flat abutment surface 82 at the front of the arcuate section 80 provides a visual queue to guide set assembly. The fitting 74 is inserted into the fitting receiver 78 until it abuts against this surface 80. The abutment surface 80 may be marked in a contrasting color to make it more obvious to the user where and how deep they are instructed to fit the fitting 74.

In some embodiments, the syringe support 18 also has a second channel transverse to and intersecting the first channel. In one embodiment, the second channel intersects the second segment of the first slot 70. In some embodiments, a selectively actuated tube clamp 84 is disposed within the second channel and is slidable therein. In the embodiments illustrated in the figures, the second channel is a second slot 86. The second slot 86 has a concave recess 88 in an upright side wall 90. The recess 88 runs lengthwise within the second slot 86 such that it is transverse to the first slot 70 and spans the entire length of the second slot 86, thus extending in a direction parallel to, or complementary with, a length of the second slot 86.

In some embodiments, the tube clamp 84 is disposed within the second slot 86. The tube clamp is illustrated individually in FIGS. 22-26. The tube clamp 84 has a tube receiver 94 which has an opening 98 that is alignable with the first slot 70 upon relative movement between the tube clamp 84 and the first slot 70. The opening 98 is large enough to accept a length of a cross-section of a tube residing within the first slot 70. The tube receiver 94 further has a clamping section 102 in communication with the opening 98 and generally transverse thereto.

The clamping section 102 has a slot-like structure having a cross-sectional area that is substantially less than a cross-sectional area of a flexible tubing 54 of the infusion set 44. Here, the term "substantially" refers to the size of the cross-sectional area of the clamping section 102 being smaller than the cross-sectional area of the tubing 54 wherein the tubing 54 is pinched and closed to restrict or eliminate a fluid flow through the tubing when the tubing 54 is located within the clamping section 102. The slot-like structure of the clamping section 102 is oriented at an angle to the upright wall 90, and, in some embodiments a right angle thereto.

Figure 2:
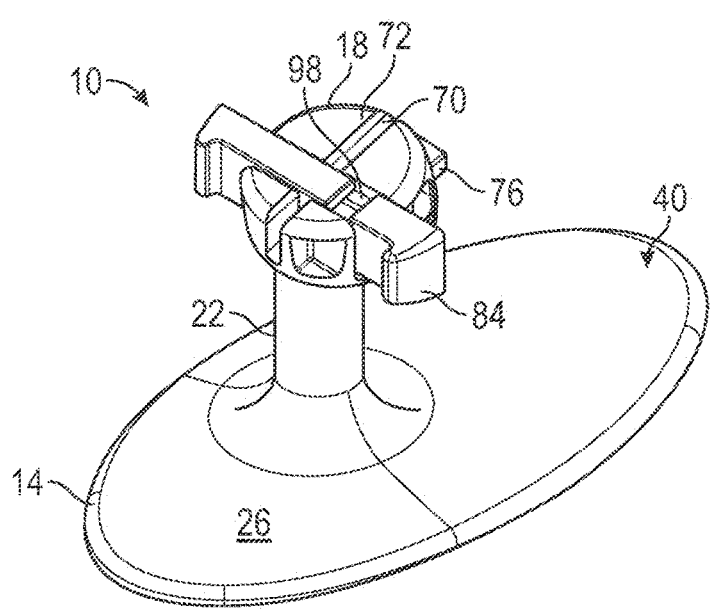
FIG. 2 is a perspective view of a syringe stabilizer according to one aspect of the invention showing a tube clamp in a closed position.
Figure 3:
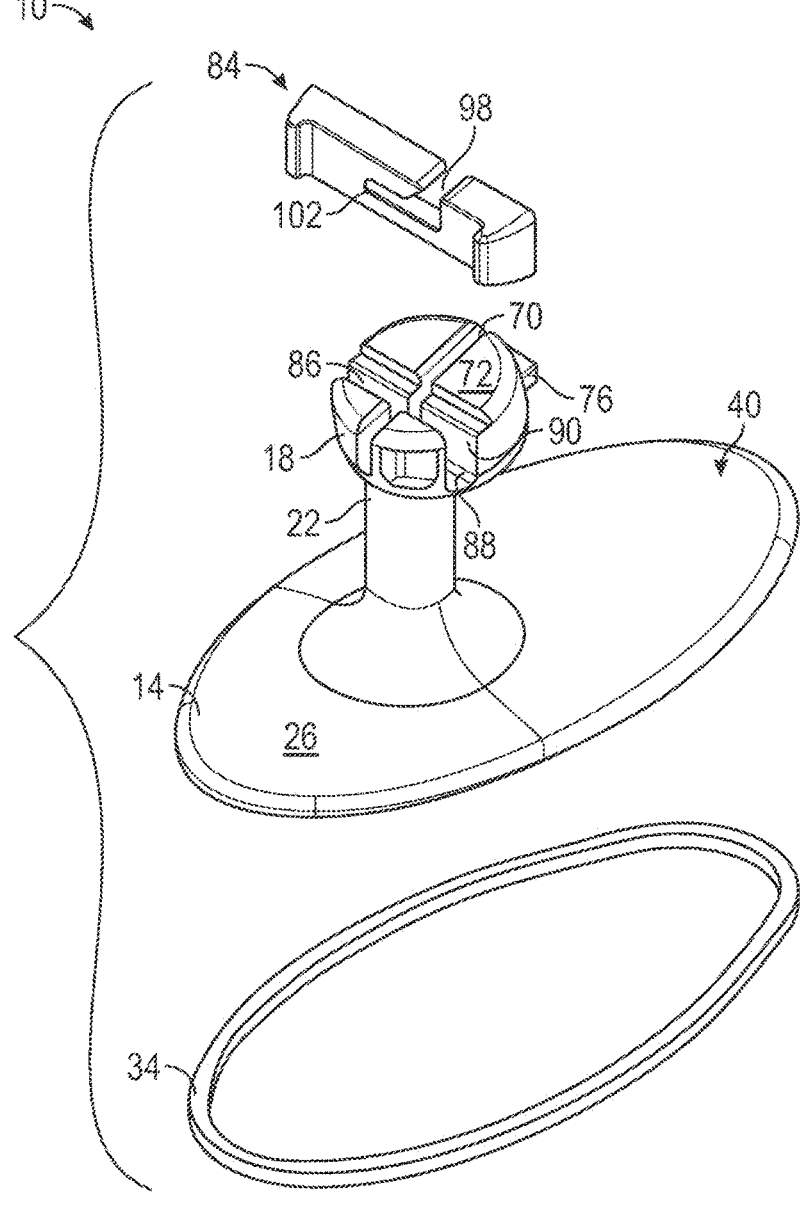
FIG. 3 is an exploded perspective view of the syringe stabilizer of FIG. 2.
Figures 7, 8, 9:
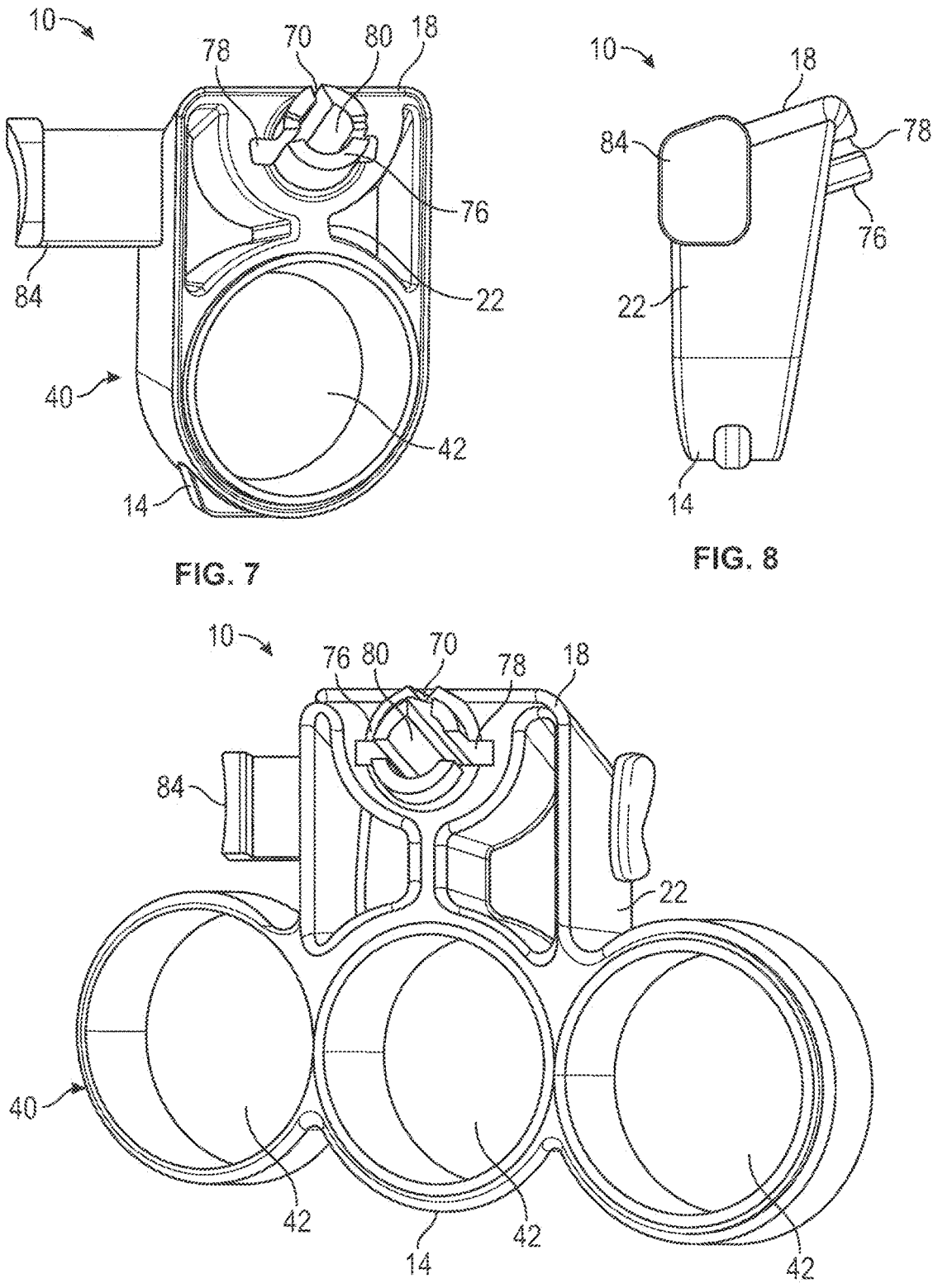
FIG. 7 is a perspective view of an alternative embodiment of a syringe stabilizer according to one aspect of the invention.
FIG. 8 is a side view of the syringe stabilizer of FIG. 7.
FIG. 9 is a perspective view of an alternative embodiment of a syringe stabilizer according to one aspect of the invention.
Figures 10, 11, 12, 13:
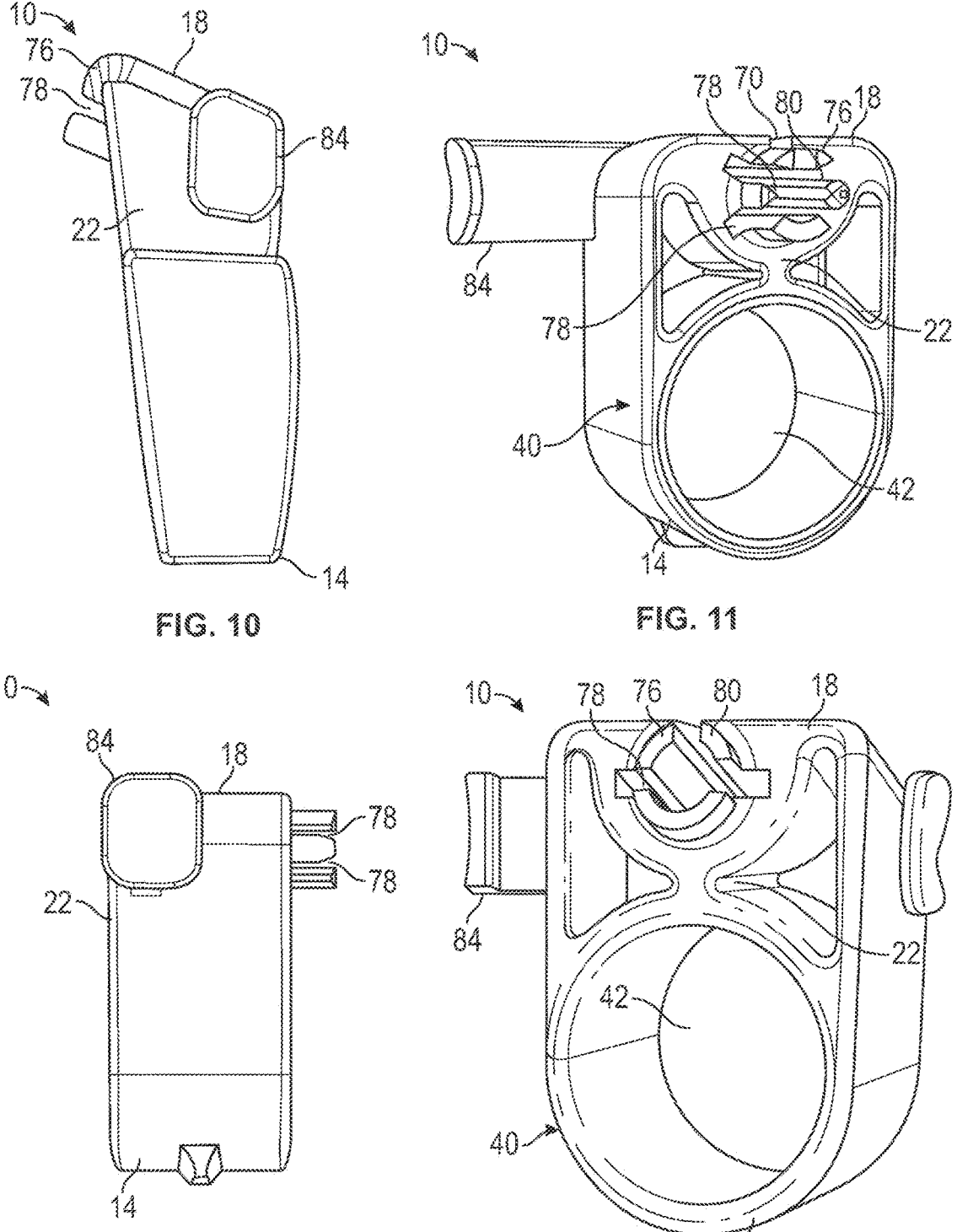
FIG. 10 is a side view of the syringe stabilizer of FIG. 9.
FIG. 11 is a perspective view of an alternative embodiment of a syringe stabilizer according to one aspect of the invention.
FIG. 12 is a side view of the syringe stabilizer of FIG. 11.
FIG. 13 is a perspective view of an alternative embodiment of a syringe stabilizer according to one aspect of the invention.
Figures 14, 15, 16, 17:
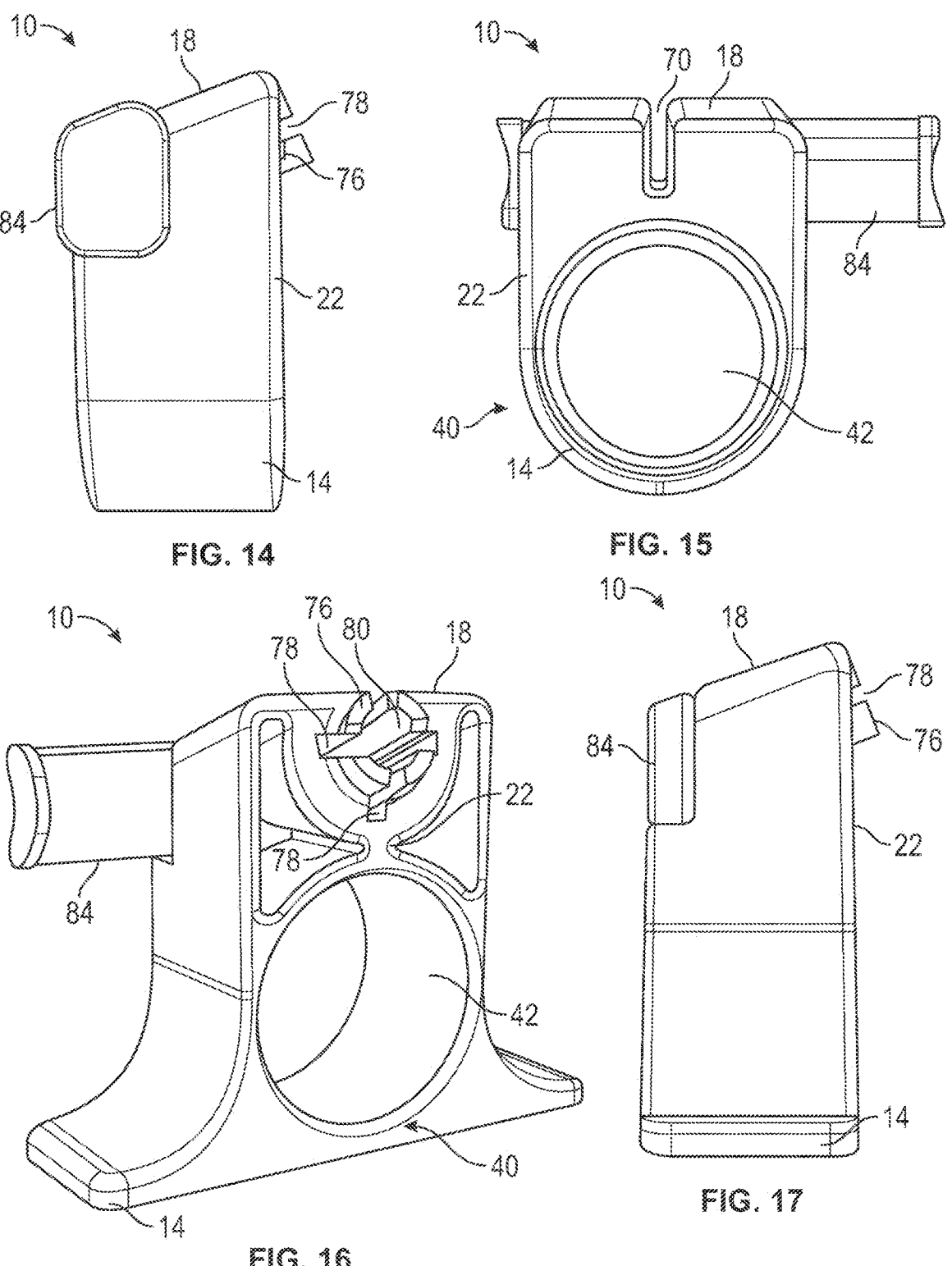
FIG. 14 is a side view of the syringe stabilizer of FIG. 13.
FIG. 15 is a front view of the syringe stabilizer of FIG. 13.
FIG. 16 is a perspective view of an alternative embodiment of a syringe stabilizer according to one aspect of the invention.
FIG. 17 is a side view of the syringe stabilizer of FIG. 16.

FIG. 1 shows the tube clamp 84 in an open condition. The therapeutic fluid within the syringe barrel 68 can flow to the user when the tube clamp 84 is in the open condition. FIG. 2 shows the tube clamp 84 transferred to the closed condition. In the closed condition, the therapeutic fluid cannot be delivered to the patient and any flow of blood from the user is also restricted because the tube 54 is pinched within the clamping section 102 of the tube clamp 84.

The tube clamp 84 has a convex keeper 104 that is retained within the concave recess 88 in the second slot 86 upright wall 90. The combination of the keeper 104 within the recess 88 maintains the tube clamp 84 in the proper location and orientation within the second slot 86 while allowing the tube clamp 84 to be within same.

In some embodiments, an angle β of an upper surface of the tube clamp 84 is generally equal to an angle of the upper surface 72 of the syringe support 18. This structural arrangement may provide a smooth transition between the tube clamp 84 within the second slot 86 of the syringe support 18 and adjacent portions of the upper surface 72 of the syringe support 18.

As illustrated in FIG. 1 and FIGS. 27-29, the syringe stabilizer 10 of FIGS. 2-6 may be used in the following manner. With the base 14 supported on a stable, generally horizontal work surface, a syringe 46 having a fluid-filled barrel 68 with a tubing 54 connected thereto by a fitting 74 is inserted with the first slot 70 while the fitting 74 is inserted within the fitting receiver 76. The tube receiver 94 of the tube clamp 84 is aligned with the first slot 70 such that tubing 54 is received therein. The tube clamp 84 is selectively actuated by sliding it within the second slot 86 in a direction transverse to the first slot 70 and opposite to the direction of the clamping section 102. Relative movement between the tube clamp 84 and the first slot 70 causes the tubing 54 to be pinched and closed. In this example, engagement between the tube 54 and the first slot 70 fixes the tubing 54 in a stationary position as the clamping section 102 engages the tubing 54 and the disparity between the cross-sectional areas of the clamping section 102 and the tubing 54 causes the tubing 54 to pinched within the clamping section 102 to prevent fluid flow within the tubing 54. This may elevate, clamp, orient, and retain the syringe 46 in a desirable position relative to a user as he/she begins the process of administering a therapy via the infusion set 44. The user's arms are now free to insert the cannula or needle 58 in a first arm 106 while manipulating the cannula 58 with a second arm 110. Thus, an arrangement of the base and syringe support positions, orients and retains the fluid-filled portion of the infusion set 44 such that a patient self-administering a therapeutic fluid is able to manipulate the tube clamp 84 and the fluid-filled portion with the first arm 106 while receiving the therapeutic fluid into the second arm 110 via the infusion set as the second arm 110 remains substantially motionless and provides a stabilizing force against the base 14. The stabilizing force must be great enough to withstand movement of the syringe stabilizer 10 along a work surface during manipulation of the tube clamp 84, in one example, sliding of the tube clamp 84 within the second slot 86, at least through actuation of the plunger 50 by the first arm 106 of the user.

For example, as illustrated in FIG. 1, with cannula 58 inserted in the second arm 110, the user may steady the base 14 by engaging some portion of the base 14, such as the ergonomic feature 40, with the second arm 110, typically a hand. Using the first arm 106, the user may selectively actuate the tube clamp 84 by creating relative movement between the tube clamp 84 and a remaining portion of the syringe support 18. Here, the user slides the tube clamp 84 within the second slot 86 to release the tube clamp 84 from pinching the tubing 54. The user may then use the first arm 106 to actuate the plunger 50 to force fluid to the cannula 58 and into the second arm 110. This allows a flow of the fluid from the delivery end 62 of the fluid-filled portion of the syringe 46 while the user's second arm/hand 110 remains substantially motionless and provides a stabilizing force against the base 18 as the user receives the flow of fluid into the second arm 110. It follows that the frictional engagement between the infusion set 44 and the first slot 70 provides a resistance force sufficient to maintain a position and an orientation of a syringe barrel 68 joined to the rigid portion of the infusion set 44 as the plunger 50 disposed within the barrel 68 is forced downwardly towards the delivery end 62 of the syringe 46.

According to one embodiment illustrated in FIGS. 1-6, the arcuate section 80 of the fitting receiver 76 accepts a portion or hub of the Luer fitting 74 of the infusion set 44 with minimal clearance. An opening in the arcuate section 80 has a chamfer edge, making it easier for users to engage/insert the Luer hub into this area. This may position the Luer approximately 2 inches to 2.75 inches (5 cm to 7 cm) above a table surface and angles it slightly up (10 to 20 degrees above horizontal), allowing users to comfortably operate an attached syringe 46 either with hand 106,110 elevated off or resting on the table surface.

Figures 18, 19, 20, 21:
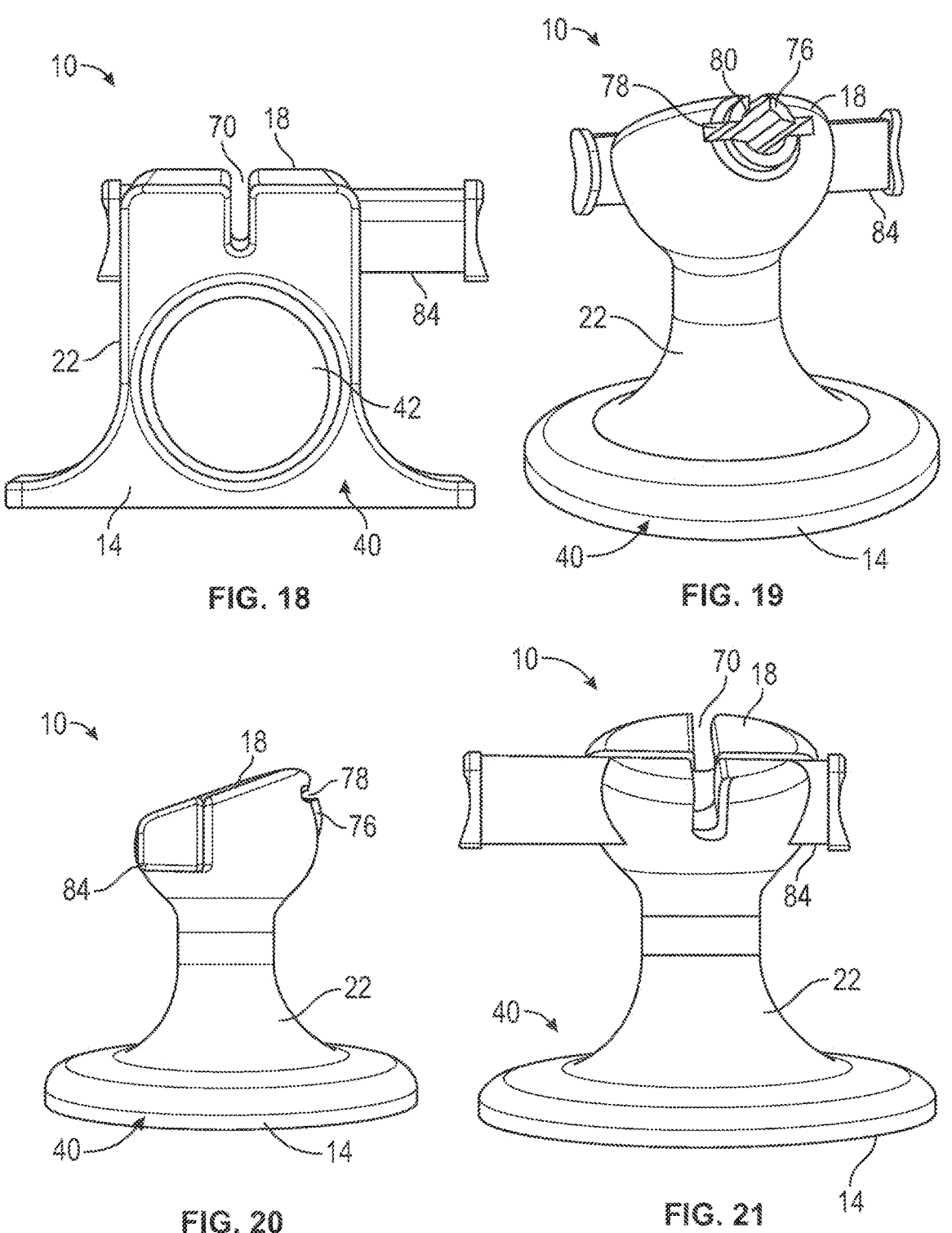
FIG. 18 is a front view of the syringe stabilizer of FIG. 16.
FIG. 19 is a perspective view of an alternative embodiment of a syringe stabilizer according to one aspect of the invention.
FIG. 20 is a side view of the syringe stabilizer of FIG. 19.
FIG. 21 is a front view of the syringe stabilizer of FIG. 19.
Figure 22:
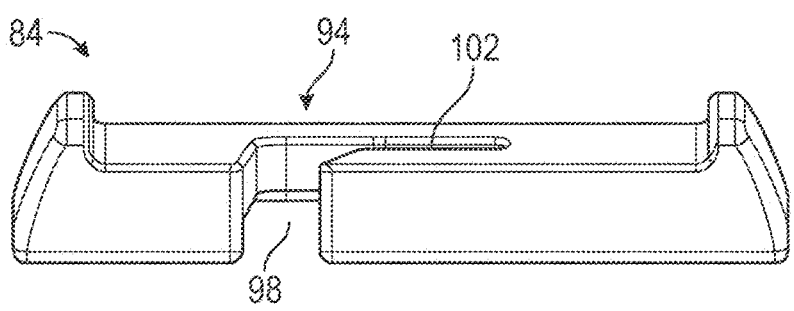
FIG. 22 is a perspective view of a selectively actuated tube clamp.
Figure 23:
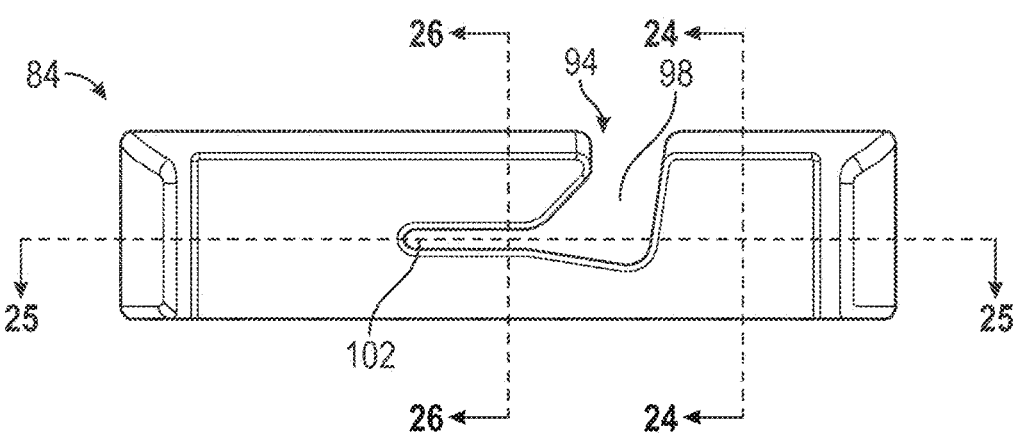
FIG. 23 is a side view of the selectively actuated tube clamp of FIG. 22.
Figure 24:
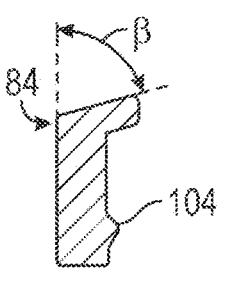
FIG. 24 is a cross-sectional view of the selectively actuated tube clamp of FIG. 23 taken along axis 24-24.
Figure 25:
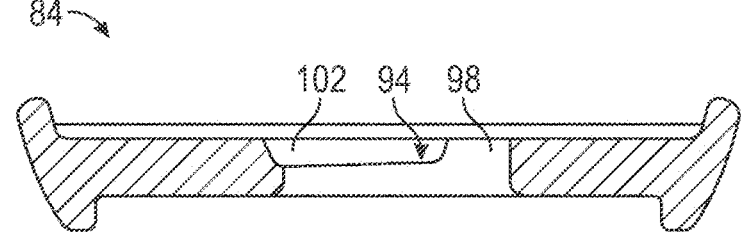
FIG. 25 is a cross-sectional view of the selectively actuated tube clamp of FIG. 23 taken along axis 25-25.
Figure 26:
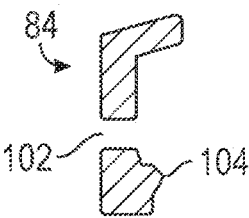
FIG. 26 is a cross-sectional view of the selectively actuated tube clamp of FIG. 23 taken along axis 26-26.
Figures 27, 28:
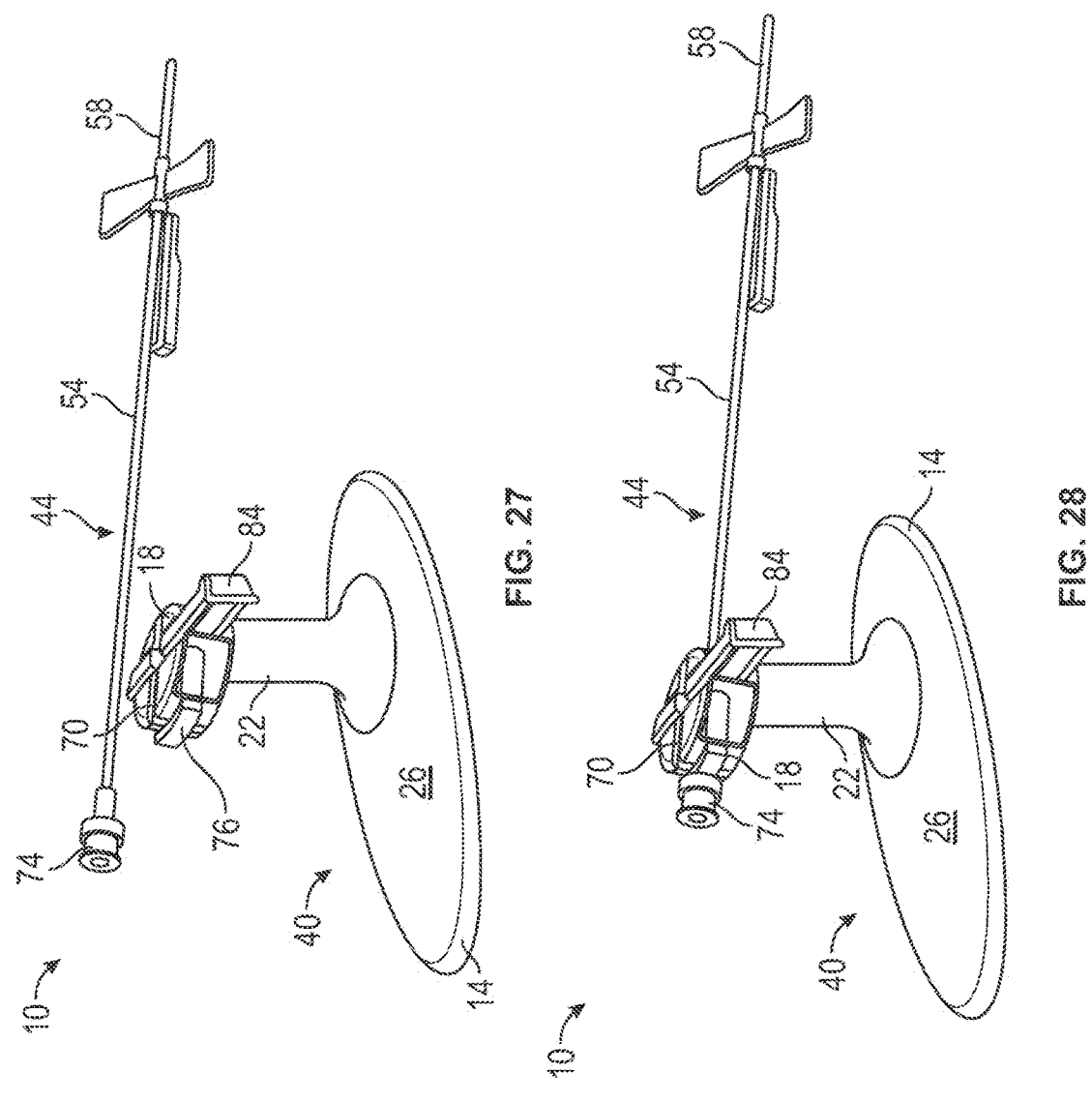
FIG. 27 is a perspective view of the syringe stabilizer of FIG. 2 with a portion of an infusion set.
FIG. 28 is a perspective view of the syringe stabilizer of FIG. 2 with a portion of an infusion set attached thereto.

Wings on the Luer fitting 74 may be received within the opposing slots 78 adjacent to the arcuate section 80 to prevent free spin (i.e. resist torque) during connection or disconnection of a syringe 46 from the fitting 74. In some cases, excessive clearance at the wing and the arcuate section 80 may increase risk of damage to wings of the fitting 74. The inventors determined through testing that the opposing slot 78 in the 3 o'clock and 9'o'clock configuration shown in, for example. FIG. 19, may be used. In other embodiments, other slot 78 configurations may be used, such as an "X" slot pattern or a "+" pattern.

The abutment surface 82 at the front of the arcuate section 80 provides a visual queue to guide use of the stabilizer 10. The Luer hub is inserted until it bottoms out against this abutment 82.

In some embodiments, the base 14 is approximately 2.36 inches×4.72 inches (6 cm×12 cm) oblong shape. This feature sits firmly on a flat table surface. It extends approximately 0.79 inches to 1.18 inches (2 cm to 3 cm) both left and right of the stem 22. A slightly larger extension of 1.18 inches to 1.97 inches (3 cm to 5 cm) behind the stem 22 improves comfort for resting the second arm 110 not operating the syringe 46 (see FIG. 30). Users may rest fingers/hand either around or beside the stem 22. An even larger extension of 2.36 inches to 3.15 inches (6 cm to 8 cm) in front of the stem 22 counterbalances weight of an attached, filled syringe 46 up to 30 cc. This also provides a large surface suitable for branding/artwork, graphical instructions, or other desired marks by pad printing, embossing, laser marking, etc. Alternatively, the second arm 110 can be placed on this section as illustrated in FIG. 1.

In some embodiments, the height of the lower base 14 may be low, and edges may be rounded, e.g., for hand comfort. The bottom surface 30 of the base 14 may incorporate a perimeter groove 38 sized to securely press-fit the elastomeric ring 34. The purpose of the ring 34 is to prevent sliding of the syringe stabilizer 10 relative to the table surface. In this embodiment. Marco Rubber part number SB1000-152 (Standard Size S152, 70A black buna square ring) may fit into the groove 38. Other ring cross-sections are possible, such as an O-ring. The ring formulation may be adjusted and/or cleaning processes may further increase tackiness, as needed. The groove height may allow full contact between an exposed square ring and the table surface. A pattern of ribs radiating from center to perimeter may be added to increase structural rigidity.

The stem 22 extends vertically from the base 14. In some embodiments, the diameter of the stem is approximately 0.40 inches to 0.79 inches (1 cm to 2 cm) and large enough for adequate structure and small enough that users are able to rest fingers around the stem 22. A stem height of 1.18 inches to 1.97 inches (3 cm to 5 cm) with <1 cm blend radius may allow adequate clearance for hands while minimizing overall size of the assembly.

In some embodiments, the syringe support 18 sits above the stem 22. The first slot 70 is chamfered opening to accept the tubing 54. The second slot 86 accepts the tube clamp 84 component, which is assembled at the manufacturing plant by a downward push that engages one-way snap fit features. Snap-fit geometry and material selections may permit easy removal of the clamp. e.g. for improved cleanability. In an alternative embodiment, the degree of engagement can be increased and snap-fit angles adjusted for a one-way snap configuration. The sides of the mount area may be substantially cored out (i.e., material removed) and drafted for improved manufacturability by injection molding.

In some embodiments, the tube clamp 84 includes a flat upper surface that sits approximately flush with upper surface 72 of the syringe support 18. The surface may allow easily readable (approximately 3 mm to 5 mm tall) printed or embossed text and symbols, such as "OPEN" and an arrow indicating the open clamp position. This wider clamp surface may also prevent incorrect clamp orientation during manufacturing. The tube clamp 84 may be molded in a bold or contrasting color from the base.

In some embodiments, the opening 98 in the tube receiver 94 is about 0.16 inches to 0.20 inches (4 mm to 5 mm). The opening 98 aligns with the first slot 70 when the clamp is in open position as illustrated in FIG. 1. The clamp opening 98 leads to the clamping section 102 which is a narrowed slot that pinches tubing (approximately 0.025 inches to 0.035 inches (0.6 mm to 0.9 mm)) when a user slides the clamp 84 fully to the closed position. Edges in this region may be blended to reduce risk of cutting tubing during clamping. Clamping may occur because flexible tubing walls are collapsed to occlude/restrict flow. Limited friction (clamp to base, clamp to tube) may allow clamp operation with little force, for example up to 8 pounds. Clamping the tubing may both block flow and prevent axial movement of the set in the stabilizer assembly.

In some embodiments, flat pads approximately 0.4 inches×0.4 inches (1 cm×1 cm) at opposite ends of the clamp 82 provide comfortable and intuitive surfaces to operate the clamp 84. Edges in this region, and all exposed edges of the stabilizer assembly, are blended for user comfort.

Polyolefin materials (polyethylene, polypropylene) or other cost-effective plastic resins (ABS, PC, polystyrene, etc.) may be used for the base 14 and clamp components. In some embodiments, sterilization is not required. High density polyethylene may be used as a material because of its cleanability, possibly even in dishwasher cycles, and general compatibility with household cleaning solutions. A variety of materials may be used for the ring component, including rubber, silicone, or thermoplastic elastomer. Similar function could be achieved by 2-shot or overmolding elastomer material to the bottom surface of the base component.

Figure 29:
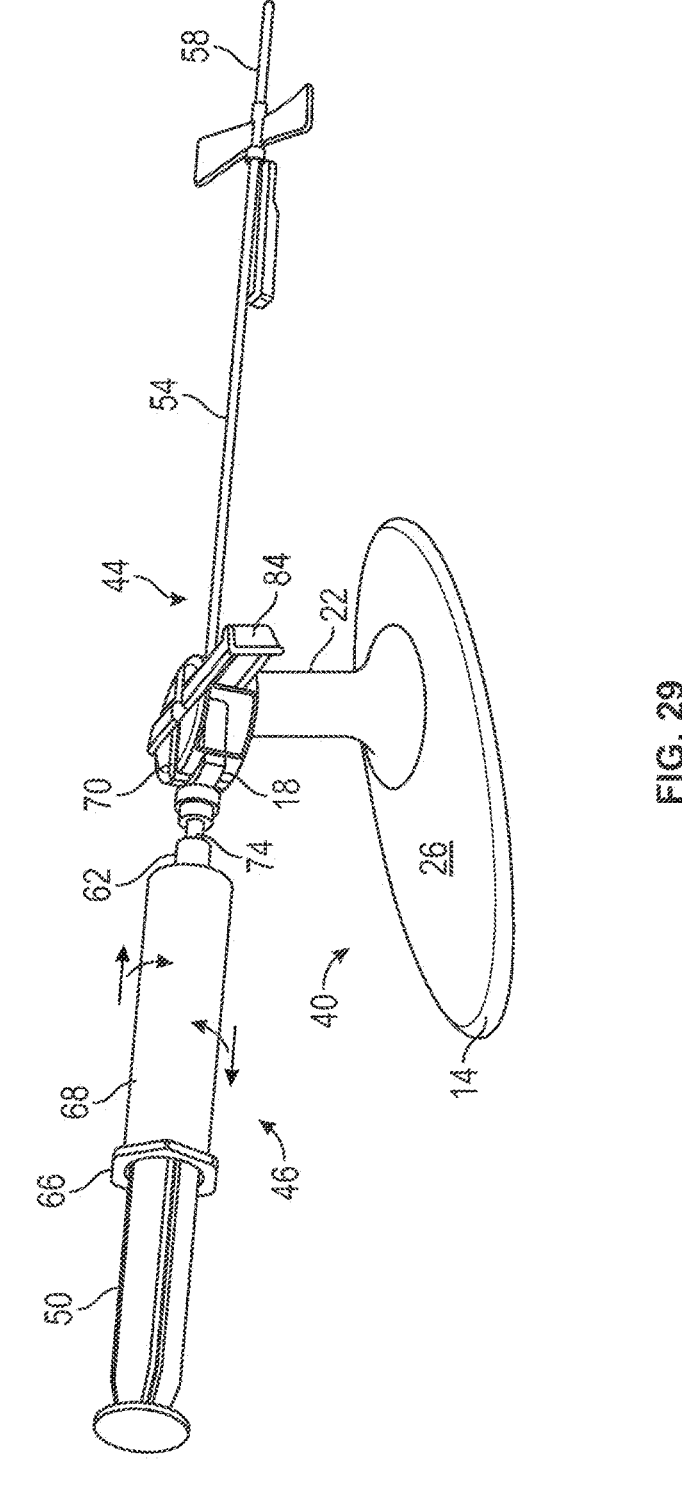
FIG. 29 is a perspective view of the syringe stabilizer of FIG. 2 with an infusion set attached thereto.

According to one aspect, the stabilizer device 10 may enhance an infusion experience by improving ease of use. As illustrated in FIG. 29, it simplifies handling/injecting multiple syringes 46 of therapeutic fluid. The arrows on FIG. 29, show that the syringe 46, threadably attached to the Luer fitting 74, can be rotated counterclockwise to remove the syringe 44 in the direction of the lower arrow outwardly from the Luer fitting 74. A new syringe 46 can be threadably attached to the Luer fitting 74 by inserting it into the Luer fitting in the direction of the upper arrow and rotating the syringe 46 in a clockwise direction.

More specifically, the syringe stabilizer 10 can be used as follows. A user slides the tube clamp 84 to an open position (shown, for example, in FIG. 27) and places the infusion set 44 tubing 54 into the first slot 70. The user slides wings of the Luer fitting 74 into the slots 78 of the fitting receiver 76 opening until the Luer fitting fits tightly within the syringe support 18.

To swap syringes 46, the tube clamp 84 is moved or slid within the second slot 86 to a closed position (shown, for example, in FIG. 2) in which the tubing 54 is pinched closed within the clamping section 102 of the tube clamp 84. The empty syringe 44 threadably attached to the Luer fitting 74 is removed from the Luer fitting 74 by rotating the syringe 46 counterclockwise with the first arm 106 while supporting or stabilizing the base 14 with the second arm 110. In this manner, the infusion set 44 cannula 58 does not need to be removed from the user's second arm 110 as the syringes 46 are swapped or changed. To connect a new or replacement syringe 46 fully loaded with a therapeutic fluid, the delivery end 62 is inserted into the Luer fitting 74 using the first arm 106 while the second arm 110 stabilizes the base 14, and it is threadably attached thereto by rotating the syringe 46 in a clockwise direction. The user then slides the tube clamp 84 to the open position using the first arm 106 while the second arm 110 is used to stabilize the base 14. The user may then use the first arm 106 to force the plunger 50 towards the delivery end 62 of the syringe 46 to force fluid to the second arm 110 while the second arm stabilizes the base 14.

According to one aspect, the stabilizer device 10 allows users to connect and disconnect multiple syringes 46 to an infusion set 44 with one hand, without directly handling the set with the other. The stabilizer effectively anchors a Luer fitting 74 of the infusion set 44 in a fixed, raised position above a table surface.

According to one aspect, the stabilizer 10 helps users minimize risk of leaks from an open set (i.e. due to blood pressure) and risk of touch contaminating an open set during syringe exchanges. In some embodiments, the stabilizer device 10 includes a tube clamp 84 that, when activated, occludes and anchors tubing 54 in the device 10. Less direct handling of the Luer fitting 74 is required for a fitting that is supported by the stabilizer 10. In some embodiments, when closed, the tube clamp prevents fluid flow through the infusion set while exposed to a pressure of about 31 mmHg (0.6 psi) at the needle.

According to one aspect, the stabilizer 10 can support weight of filled syringe 46 in a stable and hands-free manner when the user releases grip on that syringe 46.

According to one aspect, the stabilizer 10 allows adequate position of and clearance around an attached syringe 46, such that the user can comfortably operate the attached syringe 46. For example, a user could alternatively elevate a hand 106 operating the syringe 46 above a table surface or rest that hand 106 on the table during administration.

According to one aspect, the stabilizer 46 is in non-fluid contact. Therefore, this simple accessory is reusable and does not require sterilization. Stabilizer materials and design result in a lightweight, portable, cleanable, recyclable, and low-cost system.

While the specific embodiments have been illustrated and described, numerous modifications come to mind without significantly departing from the spirit of the invention, and the scope of protection is only limited by the scope of the accompanying Claims.

What is claimed is:

1. A method of using a syringe stabilizing apparatus comprising the steps of:
    moving a tube clamp to a closed position, wherein a tubing within the tube clamp is pinched closed using a first arm of a user;
    threadably detaching a first syringe from a fitting attached to the syringe stabilizing apparatus using the first arm while stabilizing a base of the syringe stabilizing apparatus with a second arm of the user such that an infusion set cannula remains attached to the second arm;
    threadably attaching a second syringe to the fitting using the first arm while the second arm stabilizes the base; and
    moving the tube clamp to an open position using the first arm while the second arm stabilizes the base.

2. The method of claim 1, wherein the tubing is disposed in a longitudinal slot of the syringe stabilizing apparatus, and wherein moving the tube clamp to the closed position comprises sliding the tube clamp through a transverse slot of the syringe stabilizing apparatus, the transverse slot intersecting the longitudinal slot.

3. The method of claim 2, wherein sliding the tube clamp through the transverse slot comprises sliding a convex keeper of the tube clamp through a concave recess of the transverse slot, the concave recess extending in a direction parallel to a length of the transverse slot.

4. The method of claim 2, wherein the longitudinal slot and the transverse slot are formed in a syringe support of the syringe stabilizing apparatus, the syringe support configured to orient a barrel of the first syringe or the second syringe at an angle above a horizontal axis such that a delivery end of the barrel of the first syringe or the second syringe is vertically offset below a plunger of the first syringe or the second syringe and the barrel of the first syringe or the second syringe is retained in an elevated position relative to the base, wherein the angle is greater than 5 degrees and less than 90 degrees.

5. The method of claim 1, wherein the tube clamp includes a tube receiver, the tube receiver comprising a clamping section and a tube receiver opening, the method further comprising placing the tubing into the tube receiver opening.

6. The method of claim 5, wherein moving the tube clamp to the closed position comprises sliding the tube clamp to pinch the tubing within the clamping section of the tube receiver.

7. The method of claim 5, wherein a cross-sectional area of the clamping section is less than a cross-sectional area of the tube receiver opening.

8. The method of claim 1, wherein moving the tube clamp to the closed position comprises restricting flow of fluid through the tubing, and wherein moving the tube clamp to the open position comprises allowing the flow of the fluid through the tubing.

9. The method of claim 1, the method further comprising attaching the fitting to the syringe stabilizing apparatus.

10. The method of claim 9, wherein attaching the fitting to the syringe stabilizing apparatus comprises inserting portions of the fitting into a fitting receiver of the syringe stabilizing apparatus.

11. The method of claim 10, wherein the fitting receiver is a removable fitting receiver, the method further comprising attaching the removable fitting receiver to the syringe stabilizing apparatus.

12. The method of claim 1, further comprising the step of:
forcing a plunger of the second syringe towards a delivery end of the second syringe using the first arm to force a fluid to the second arm via the infusion set cannula while the second arm stabilizes the base.

13. The method of claim 12, wherein the fluid comprises a therapeutic for treating hemostatic disorder caused by a liver disease.

14. The method of claim 12, wherein the fluid comprises a therapeutic for treating a bleeding disorder.

15. The method of claim 14, wherein the bleeding disorder is a deficiency in a coagulation factor.

16. The method of claim 15, wherein the coagulation factor is a Factor V, a Factor VIII, a Factor IX, a Factor XI, or a von Willebrand Factor.

17. The method of claim 14, wherein the therapeutic is a recombinant Factor VIII (rFVIII), a procoagulant bypassing agent, or a recombinant von Willebrand Factor (rVWF).

18. Method of claim 1, wherein the syringe stabilizing apparatus comprises:

a syringe support vertically disposed above the base, the syringe support configured to elevate the first syringe or the second syringe vertically above the base and to orient a delivery end of the first syringe or the second syringe upwardly relative to a horizontal plane to take advantage of a gravitational effect on a fluid during delivery of the fluid from the first syringe or the second syringe to the user, the syringe support comprising:
a first retainer having an opening configured to receive and retain a rigid portion of an infusion set therein without further user intervention; and
the tube clamp, wherein the tube clamp is operatively aligned with the first retainer, and wherein the tubing extends from the rigid portion of the infusion set through the tube clamp,
wherein the tube clamp is releasable by the first arm of the user to allow flow of the fluid from the first syringe or the second syringe while the second arm of the user remains substantially motionless and stabilizes the base as the user receives the fluid from the first syringe or the second syringe into the second arm.

19. The method of claim 1, wherein the base of the syringe stabilizing apparatus is portable and has an engagement surface configured to support the syringe stabilizing apparatus against a work surface and an ergonomic handset, and wherein the syringe stabilizing apparatus further comprises:
a syringe support vertically disposed above the base, the syringe support comprising:
a first channel having a lengthwise opening configured to accept the fitting and retain the fitting therein, the syringe support configured to support the first syringe or the second syringe at an angle above a horizontal axis such that a delivery end of the first syringe or the second syringe is vertically offset below a plunger of the first syringe or the second syringe such that the first syringe or the second syringe is retained in an elevated position relative to the base, wherein the angle is greater than 5 degrees and less than 90 degrees;
a second channel transverse to and intersecting the first channel;
the tube clamp, wherein the tube clamp is disposed within the second channel and slidable therein, the tube clamp comprising a tube receiver having an opening alignable with the first channel and a clamping section generally transverse to the first channel, the clamping section having a cross-sectional area configured for pinching the tubing as the tube clamp is slid within the second channel in a direction transverse to the first channel.

* * * * *